United States Patent [19]

Norman et al.

[11] Patent Number: 5,684,205

[45] Date of Patent: Nov. 4, 1997

[54] USE OF SUBSTITUTED CYCLOPENTANE-DI- AND -TRIONES

[75] Inventors: Peter Norman, Burnham; Roderick L. Hall, Addlestone; Graham A. Place, Thame, all of England; Graham Holmwood; Gabriele Bräunlich, both of Wuppertal, Germany

[73] Assignee: Bayer Aktiengesellschaft, Leverkusen, Germany

[21] Appl. No.: 525,871

[22] Filed: Sep. 8, 1995

[30] Foreign Application Priority Data

Sep. 16, 1994 [GB] United Kingdom ............ 9418762

[51] Int. Cl.$^6$ .................................. C07C 45/45
[52] U.S. Cl. .................. 568/316; 514/677; 514/680
[58] Field of Search ............... 568/316; 514/677, 514/680

[56] References Cited

U.S. PATENT DOCUMENTS 3,592,921  7/1971  Wagner et al. .

FOREIGN PATENT DOCUMENTS 3239368  4/1984  Germany .
1341650  of 1974  United Kingdom .

OTHER PUBLICATIONS

Rehse et al;Arch.Pharm. (Weinheim, Ger.);317(9);781–9 1984.

W. Wislicenus, et al., Justus Liebigs Annalen Der Chemie, vol. 436, pp. 101 –112, (1924).

K. Rehse, et al., Arch. Pharm., vol. 317, pp. 781–789, (1984).

L.D. Foland, et al., J. Am. Chem. Soc., vol. 111, No. 3, pp. 975 –989, (1989).

*Primary Examiner*—C. Warren Ivy
*Assistant Examiner*—Sreenivas Padmanabhan
*Attorney, Agent, or Firm*—Sprung Kramer Schaefer & Briscoe

[57] ABSTRACT

The invention relates to the use of substituted cyclopentane-diones and cyclopentane-triones for the preparation of medicaments which as chloride channel blockers are suitable for controlling airway diseases, secretory diarrhea and inflammatory diseases.

10 Claims, No Drawings

USE OF SUBSTITUTED CYCLOPENTANE- DI- AND -TRIONES

The invention relates to the use of substituted cyclopentane- di- and -triones as medicaments, in particular as chloride channel blockers, new active compounds and processes for their preparation.

It is known that 1,2,4-cyclopentanetrione derivatives have an anticoagulant action (Arch. Pharm. (Weinheim Ger.) (1984), 317 (9), 781-9).

4-Cyclopentene-1,3-dione are described in the publication J. Am. Chem. Soc. (1989), 111 (3), 975-89.

4-Hydroxy-5-aryl-cyclopent-4-ene-1,3-dione having anticoagulant action are described in DE 32 39 368.

It is well known that chloride ion movement through cell membranes plays a significant role in maintaining the electrogenic potential of many cell types. Chloride ion movements may be controlled by either transport proteins or by (various) chloride channel proteins. Airway epithelial cells contain chloride channels which upon activation provide a selective export of chloride ions. This is important in a number of physiological processes. A number of channel proteins have now been cloned and analysis of their protein sequence has shown them to contain a number of transmembrane domains indicative of their role in maintaining membrane potential. The best documented chloride channel protein is the cystic fibrosis transmembrane regulator (CFTR). Chloride channels have a significant function in variety of physiological processes.

It has been found that substituted cyclopentane- di- and -triones of the general formula (I)

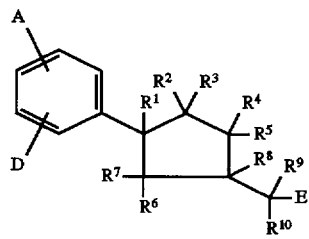

(I)

in which

A and D are identical or different and represent hydrogen, halogen, nitro, phenyl or straigth-chain or branched alkyl having up to 8 carbon atoms or represent a group of the formula $-NR^{11}R^{12}$, $-CO_2R^{13}$ or $-O(CH_2)_a(CO_2)_bR^{14}$ in which $R^{11}$ and $R^{12}$ are identical or different and denote hydrogen, phenyl or straight-chain or branched alkyl having up to 6 carbon atoms, $R^{13}$ denotes hydrogen or straight-chain or branched alkyl having up to 8 carbon atoms, a denotes a number 0, 1,2, 3 or 4, b denotes a number 0 or 1, $R^{14}$ has the abovementioned meaning of $R^{13}$ and is identical or different to that or denotes phenyl, $R^1$ represents hydrogen, $R^2$ and $R^3$, $R^4$ and $R^5$ and/or $R^6$ and $R^7$ represent a residue of the formula =O, or two of the pairs have the abovementioned meaning and both substitutents of the remaining pair, $R^2$ and $R^3$ or $R^4$ and $R^5$ or $R^6$ and $R^7$ represent hydrogen, or $R^1$ and $R^2$ or $R^1$ and $R^7$ or $R^2$ and $R^4$ together represent a double bond and in these cases, $R^3$, $R^5$ and $R^6$ respectively represent hydrogen, hydroxyl or a straight-chain or branched alkoxy having up to 6 carbon atoms, $R^8$ and $R^9$ represent hydrogen, or $R^8$ and $R^9$ together represent a double bond, $R^{10}$ has the abovementioned meaning of A or D and is identical or different to that, E represents a 5 to 7 membered, aromatic heterocycle having up to 3 heteroatoms from the series comprising N, S and O and to which a phenyl ring can be fused, or represents aryl having up to 6 to 10 carbon atoms and wherein all rings are optionally monosubstituted to trisubstituted by identical or different substitutents from the series comprising halogen, nitro, trifluoromethyl, phenyl or straight-chain or branched alkyl having up to 6 carbon atoms or by a group of the formula $-NR^{15}R^{16}$, $-CO_2R^{17}$ or $-O(CH_2)_d-(CO_2)_eR^{18}$ in which $R^{15}$ and $R^{16}$ have the abovementioned meaning of $R^{11}$ and $R^{12}$ and are identical or different to that, $R^{17}$ has the abovementioned meaning of $R^{13}$ and is identical or different to that $R^{18}$ has the above mentioned meaning of $R^{14}$ and is identical or different to that, d denotes a number 0, 1, 2, 3 or 4, e denotes a number 0 or 1, and their isomers and salts, surprisingly have a strong chloride channel blocker action and are thus suitable for use in the control of airway disease, secretory diarrhoea and inflammatory diseases.

Preferably used compounds are those of the general formula (I), in which

A and D are identical or different and represent hydrogen, fluorine, chlorine, bromine, nitro, phenyl or straigth-chain or branched alkyl having up to 6 carbon atoms or represent a group of the formula $-NR^{11}R^{12}$, $-CO_2R^{13}$ or $-O(CH_2)_a(CO_2)_bR^{14}$ in which $R^{11}$ and $R^{12}$ are identical or different and denote hydrogen, phenyl or straight-chain or branched alkyl having up to 4 carbon atoms, $R^{13}$ denotes hydrogen or straight-chain or branched alkyl having up to 6 carbon atoms, a denotes a number 0, 1,2, 3 or 4, b denotes a number 0 or 1, $R^{14}$ has the abovementioned meaning of $R^{13}$ and is identical or different to that or denotes phenyl, $R^1$ represents hydrogen, $R^2$ and $R^3$, $R^4$ and $R^5$ and/or $R^6$ and $R^7$ represent a residue of the formula =O, or two of the pairs have the abovementioned meaning and both substitutents of the remaining pair, $R^2$ and $R^3$ or $R^4$ and $R^5$ or $R^6$ and $R^7$ represent hydrogen or $R^1$ and $R^2$ or $R^1$ and $R^7$ or $R^2$ and $R^4$ together represent a double bond and in these cases $R^3$, $R^5$ and $R^6$ respectively represent hydrogen hydroxyl or a straight-chain or branched alkoxy having up to 4 carbon atoms, $R^8$ and $R^9$ represent hydrogen, or $R^8$ and $R^9$ together represent a double bond or $R^{10}$ has the abovementioned meaning of A or D and is identical or different to that, E represents thienyl, pyridyl, naphthyl or phenyl, which are optionally monosubstituted to trisubstituted by identical or different substitutents from the series comprising fluorine, chlorine, bromine, nitro, trifluoromethyl, phenyl or straight-chain or branched alkyl having up to 4 carbon atoms or by a group of the formula —$NR^{15}R^{16}$, —$CO_2R^{17}$ or —$O(CH_2)_d$—$(CO_2)_eR^{18}$,
in which
$R^{15}$ and $R^{16}$ have the abovementioned meaning of $R^{11}$ and $R^{12}$ and are identical or different to that,
$R^{17}$ has the abovementioned meaning of $R^{13}$ and is identical or different to that
$R^{18}$ has the above mentioned meaning of $R^{14}$ and is identical or different to that,
d denotes a number 0, 1, 2, 3 or 4,
e denotes a number 0 or 1,
and their isomers and salts, Particularly preferably used compounds are those of the general formula (I),
in which
A and D are identical or different and represent hydrogen, fluorine, chlorine, bromine, nitro, phenyl or straigth-chain or branched alkyl having up to 5 carbon atoms or
represent a group of the formula —$NR^{11}R^{12}$, —$CO_2R^{13}$ or —$O(CH_2)_a(CO_2)_bR^{14}$,
in which
$R^{11}$ and $R^{12}$ are identical or different and denote hydrogen, phenyl or straight-chain or branched alkyl having up to 3 carbon atoms,
$R^{13}$ denotes hydrogen or straight-chain or branched alkyl having up to 5 carbon atoms,
a denotes a number 0, 1,2, 3 or 4,
b denotes a number 0 or 1,
$R^{14}$ has the abovementioned meaning of $R^{13}$ and is identical or different to that or denotes phenyl,
$R^1$ represents hydrogen,
$R^2$ and $R^3$, $R^4$ and $R^5$ and/or $R^6$ and $R^7$ represent a residue of the formula =O, or two of the pairs have the abovementioned meaning and both substituents of the remaining pair, $R^2$ and $R^3$ or $R^4$ and $R^5$ or $R^6$ and $R^7$ represent hydrogen,
or
$R^1$ and $R^2$ or $R^1$ and $R^7$ or $R^2$ and $R^4$ together represent a double bond and in these cases,
$R^3$, $R^5$ and $R^6$ respectively represent hydrogen hydroxyl or a straight-chain or branched alkoxy having up to 3 carbon atoms,
$R^8$ and $R^9$ represent hydrogen,
or
$R^8$ and $R^9$ together represent a double bond,
$R^{10}$ has the abovementioned meaning of A or D and is identical or different to that,
E represents thienyl, pyridyl, naphthyl or phenyl, which are optionally monosubstituted to trisubstituted by identical or different substitutents from the series comprising fluorine, chlorine, bromine, trifluoromethyl, nitro, phenyl or straight-chain or branched alkyl having up to 4 carbon atoms or by a group of the formula —$NR^{15}R^{16}$, —$CO_2R^{17}$ or —$O(CH_2)_d$—$(CO_2)_eR^{18}$,
in which
$R^{15}$ and $R^{16}$ have the abovementioned meaning of $R^{11}$ and $R^{12}$ and are identical or different to that,
$R^{17}$ has the abovementioned meaning of $R^{13}$ and is identical or different to that
$R^{18}$ has the above mentioned meaning of $R^{14}$ and is identical or different to that,
d denotes a number 0, 1, 2, 3 or 4,
e denotes a number 0 or 1,
and their isomers and salts.

Very particulary preferably used are compounds of the general formula (I),
in which
A and D are identical or different and represent hydrogen, phenyl, chlorine or methoxy.

The invention additionally relates to new compounds of the general formula (I),
in which
A and D are identical or different and represent hydrogen, halogen, nitro, phenyl or straigth-chain or branched alkyl having up to 8 carbon atoms or represent a group of the formula —$NR^{11}R^{12}$, —$CO_2R^{13}$ or —$O(CH_2)_a(CO_2)_bR^{14}$
in which
$R^{11}$ and $R^{12}$ are identical or different and denote hydrogen, phenyl or straight-chain or branched alkyl having up to 6 carbon atoms,
$R^{13}$ denotes hydrogen or straight-chain or branched alkyl having up to 8 carbon atoms,
a denotes a number 0, 1,2, 3 or 4,
b denotes a number 0 or 1,
$R^{14}$ has the abovementioned meaning of $R^{13}$ and is identical or different to that or denotes phenyl,
$R^1$ represents hydrogen,
$R^2$ and $R^3$, $R^4$ and $R^5$ and/or $R^6$ and $R^7$ represent a residue of the formula =O, or two of the pairs have the abovementioned meaning and both substituents of the remaining pair, $R^2$ and $R^3$ or $R^4$ and $R^5$ or $R^6$ and $R^7$ represent hydrogen,
or
$R^1$ and $R^2$ or $R^1$ and $R^7$ or $R^2$ and $R^4$ together represent a double bond and in these cases,
$R^3$, $R^5$ and $R^6$ respectively represent hydrogen hydroxyl or a straight-chain or branched alkoxy having up to 6 carbon atoms,
$R^8$ and $R^9$ represent hydrogen,
or
$R^8$ and $R^9$ together represent a double bond,
$R^{10}$ has the abovementioned meaning of A or D and is identical or different to that,
E represents a 5 to 7 membered, aromatic heterocycle having up to 3 heteroatoms from the series comprising N, S and O and to which a phenyl ring can be fused, or
represents aryl having up to 6 to 10 carbon atoms and wherein all rings are optionally monosubstituted to trisubstituted by identical or different substitutents from the series comprising halogen, nitro, trifluoromethyl, phenyl or straight-chain or branched alkyl having up to 6 carbon atoms or by a group of the formula —$NR^{15}R^{16}$, —$CO_2R^{17}$ or —$O(CH_2)_d$—$(CO_2)_eR^{18}$,
in which
$R^{15}$ and $R^{16}$ have the abovementioned meaning of $R^{11}$ and $R^{12}$ and are identical or different to that,
$R^{17}$ has the abovementioned meaning of $R^{13}$ and is identical or different to that
$R^{18}$ has the above mentioned meaning of $R^{14}$ and is identical or different to that,
d denotes a number 0, 1, 2, 3 or 4,
e denotes a number 0 or 1,
and their tautomers, racemates, enantiomers, diastereomers and salts,
with the exception of
1,2,4-cyclopentanetrione, 3-[(4-chlorophenyl)methyl]-5-phenyl, 1,2,4-cyclopentanetrione, 3-[(4-chloro-3-nitrophenyl)methyl]-5-phenyl, 1,2,4-cyclopentanetrione, 3-[

(4-chlorophenyl)methylene]-5-phenyl, 4-cyclopentene-1,3-dione, 4-ethoxy-5-phenyl-2-(phenylmethylene)-(Z) and (E) 4-cyclopentene-1,3-dione, 2-[(4-chlorophenyl)methyl]-4-hydroxy-5-phenyl 4-cyclopentene-1,3-dione, 2-[4-(chlorphenyl)methylene)-4-hydroxy-5-phenyl 2-(4-chloro-3-nitrobenzyliden)-4-hydroxy-5-phenyl-cyclopent-4-ene-1,3-dion 3-(4-nitro-benzylidene)-5-phenyl-cyclopentane-1,2,4-trione 3-(4-methyl-benzylidene)-5-phenyl-4-cyclopentane-1,2,4-trione 3-benzylidene-5-phenyl-cyclopentane-1,2,4-trione.

The substituted cyclopentane-di- and -triones of the general formulae (I) according to the invention can also be present in the form of their salts. In general, salts with organic or inorganic bases or acids may be mentioned here. Preferred are physiologically acceptable salts.

Physiologically acceptable salts are preferred in the context of the present invention. Physiologically acceptable salts of the substituted 1,2,4-cyclopentane-trione and 4-cyclopentene-1,3-dione (I/Ia) can be metal or ammonium salts of the substances according to the invention, which contain a free carboxylic group. Those which are particularly preferred are, for example, sodium, potassium, magnesium or calcium salts, and also ammonium salts which are derived from ammonia, or organic amines, such as, for example, ethylamine, di- or tri- ethylamine, di- or triethanolamine, dicyclohexylamine, dimethylaminoethanol, arginine, lysine or ethylenediamine.

The compounds according to the invention can exist in stereoisomeric forms which either behave as image and mirror image (enantiomers), or which do not behave as image and mirror image (diastereomers). The invention relates both to the antipodes and to the racemate forms, as well as the diastereomer mixtures. The racemate forms, like the diastereomers, can be separated into the stereoisometrically uniform constituents in a known manner.

Double bonds can be either cis/trans, E or Z configurated or E/Z-mixture.

As heterocycles the following are mentioned as preferred: thienyl, furyl, pyrrolyl, pyridyl, pyrimidyl, quinolyl, isoquinolyl, thiazolyl, oxazolyl, benzoxazolyl, isoxazolyl, imidazolyl, benzimidazolyl or indolyl.

Processes for the preparation of the compounds of the general formulae (I) according to the invention have additionally been found, characterized in that

[A] compounds of the general formula (II)

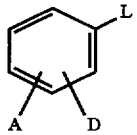 (II)

in which

A and D have the meaning already given,
and

L stands for the residue

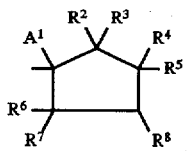

are reacted with compounds of the general formulae (III) or (IIIa)

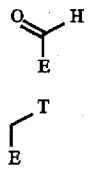 (III)

 (IIIa)

in which

E has the meaning given,
and

T denotes halogene, preferably chlorine, likewise in the presence of an inert solvent and if appropriate in presence of a base and/or an auxiliary, or

[B] in the case of the triones and their tautomeres compounds of the general formula (IV)

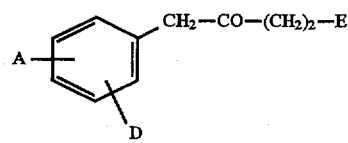 (IV)

in which

A, D and E have the abovementioned meaning, are reacted with diethyloxalate/NaOC$_2$H$_5$ by cyclisation after decarboxylation, and if appropriate in the case of R$^8$/R$^9$=hydrogen, compounds of the general formulae (I) with a corresponding double bond are hydrogenated and in the case of R$^3$, R$^5$ or R$^6 \neq$OH, the corresponding hydroxyl compounds are etherified, The processes according to the invention can be illustrated by way of example by the following reaction scheme:

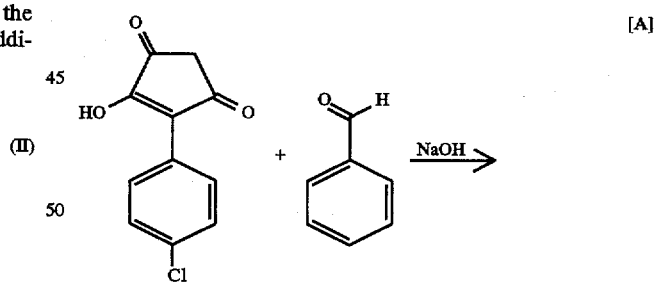 [A]

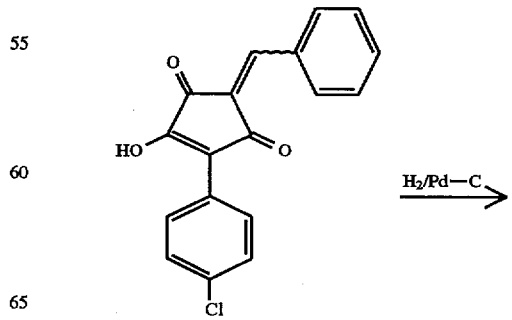

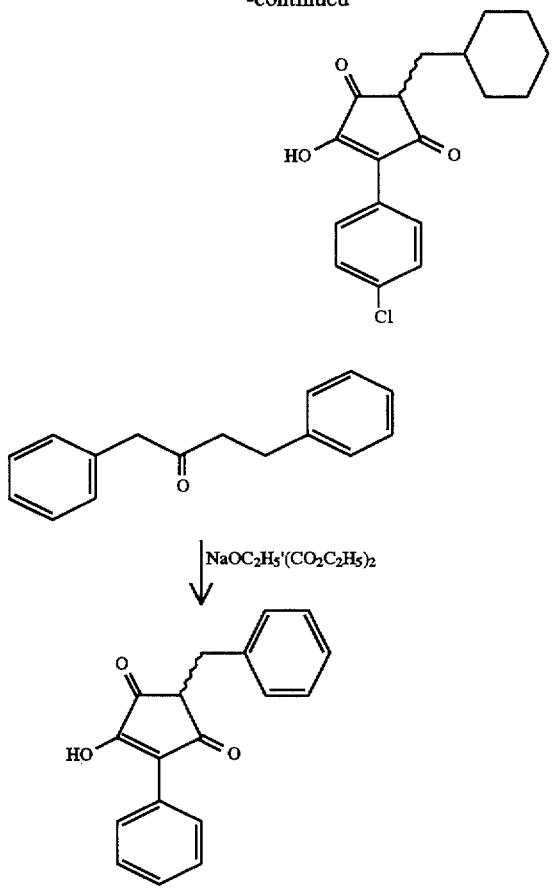

Suitable solvents are generally customary organic solvents which do not change under the reaction conditions. These include ethers such as diethyl ether, dioxane or tetrahydrofurane, acetone, dimethylsulfoxide, dimethylformamide or alcohols such as methanol, ethanol, propanol or halogenohydrocarbons such as dichlormethane, trichloromethane or tetrachloromethane. Methanol and dichloromethane are preferred.

Suitable bases are generally inorganic or organic bases. These preferably include alkali metal hydroxides such as, for example, sodium hydroxide, sodium hydrogencarbonate or potassium hydroxide, alkaline earth metal hydroxides such as, for example, barium hydroxide, alkali metal carbonates such as sodium carbonate, potassium carbonate, alkaline earth metal carbonates such as calcium carbonate, or alkaline metal or alkaline earth metal alkoxides such as sodium methoxide or potassium methoxide, sodium ethoxide or potassium ethoxide or potassium tert.butoxide, or organic amines (trialkyl($C_1$-$C_6$)amines) such as triethylamine, or heterocycles such as 1,4-diazabicyclo[2.2.2]octane (DABCO), 1,8-diazabicyclo[5.4.0]undec-7-ene (DBU), or amides such as sodium amides, lithium butyl amide or butyllithium, pyridine or methylpiperidine. It is also possible to employ alkali metals, such as sodium or its hydrides such as sodium hydride, as bases. Potassium carbonate, triethylamine, sodium hydrogencarbonate and sodiumhydroxide are preferred.

The base is employed in an amount from 1 mol to 10 mol, preferably from 1.0 mol to 4 mol, relative to 1 mol of the compounds of the general formulae (III) and (IIIa).

The processes according to the invention are in general carried out in a temperature range from −20° C. to +150° C., preferably from 50° C. to 120° C.

The process is generally carried out at normal pressure. However, it is also possible to carry out it at elevated pressure or at reduced pressure (for example in a range from 0.5 to 5 bar).

Auxiliaries employed are preferably condensing agents which can also be bases, in particular if the carboxyl group is present activated as the anhydride. Those preferred here are the customary condensing agents such as carbodiimides e.g. N,N'-diethyl-, N,N'-diisopropyl- and N,N'-dicyclohexylcarbodiimide, N-(3-dimethylamino-isopropyl)-N'-ethyl-carbodiimide hydrochloride, N-cyclohexyl-N'-(2-morpholinoethyl)-carbodiimide metho-p-toluenesulphonate, or carbonyl compounds such as carbonyldiimidazole, or 1,2-oxazolium compounds such as 2-ethyl-5-phenyl-1,2-oxazolium-3-sulphate or 2-tert.butyl-5-methyl-isoxazolium perchlorate, or acylamino compounds such as 2-ethoxy-1-ethoxycarbonyl-1,2-dihydro-quinoline, or propanephosphonic anhydride, or isobutyl chloroformate, or benzotriazolyloxy-tris(dimethylamino)-phosphonium hexafluorphosphate or 1-hydroxybenzotriazole.

Additionally, for example, alkali metal carbonates, e.g. sodium carbonate or hydrogen carbonate or potassium carbonate or hydrogen carbonate, or organic bases such as trialkylamines, e.g. triethylamine, ethyldiisopropylamine, N-ethylmorpholine, N-methylpiperidine or N-methylmorpholine can be employed. N-Methylmorpholine is preferred.

The etherication of the compounds according to the invention ($R^{3''}/R^{5''}/R^{7''}(L)\ne OH$) is carried out using one of the abovementioned alkylating agents in the presence of one of the abovementioned solvents and bases, preferably using potassium tert.butoxide or sodium hydride.

The reactions are in general carried out in a temperature range from −20° C. to +80° C., preferably from 0° C. to +60° C.

In general, the reaction is carried out at normal pressure. However, it is possible to work at reduced pressure or at elevated pressure (e.g. from 0.5 to 5 bar).

Hydrogenation is carried out in a known manner by transfer hydrogenation, for example using Pd/C in organic solvents such as ethers, e.g. tetrahydrofuran or dioxane, or alcohols e.g. methanol, ethanol or isopropanol.

Hydrogenation is in general carried out in a temperature range from 0° C. to 80° C., preferably from 0° C. to 40° C.

In general, hydrogenation is carried out at elevated pressure from 2 bar to 8 bar, preferably from 3 to 5 bar.

Suitable acids for individual process steps are in general protic acids such as, for example, hydrochloric or sulphuric acids. Sulphuric and hydrochloric acids are preferably employed.

The acid is in general employed in an amount from 1 mol to 20 mol, preferably from 1 mol to 5 mol, in each case relative to 1 mol of the reactant.

The compounds of the general formula (II) are known or can be prepared
a) in the case of

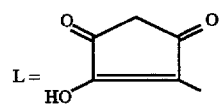

by firstly reacting compounds of the formula (V)

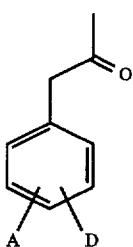

in which
A and D have the abovementioned meaning,
with diethyloxalate in the presence of sodium ethoxide to give compounds of the general formula (VI)

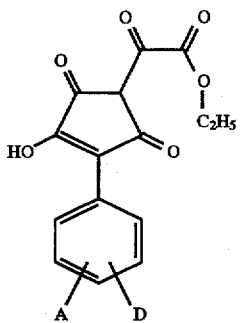

in which
A and D have the abovementioned meaning and following decarboxylation and cyclisation in analogy to the above described process [A], and
b) in the cases in which L denotes the residues

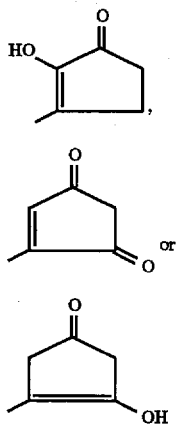

first the trione of the general formula (IIa)

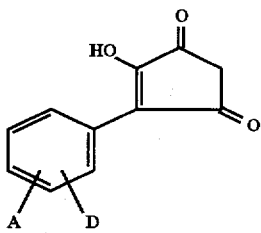

in which
A and D have the abovementioned meaning are reacted with $(C_2H_5O)_3CH$ to the corresponding acetal of the general formula (VII)

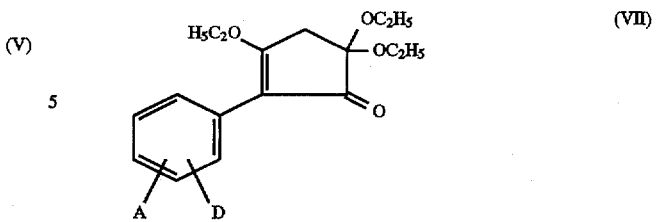

in which
A and D have the abovementioned meaning and in a last step are reduced in inert solvents selectively.

Reductions of the acetals is in general carried out using reducing agents such as, for example lithium aluminium hydrides and aluminium alkyls. Preferred are in the case of hydroxyl substituted cyclopentene derivatives lithium aluminium-hydride and in the other case DIBAL.

Suitable solvents are one of the abovementioned ethers for example tetrahydrofuran, dioxane or diethylether.

The reactions are in general carried out in a temperature range from $-20°$ C. to $+80°$ C., preferably from $0°$ C. to $+60°$ C.

In general, the reaction is carried out at normal pressure. However, it is possible to work at reduced pressure or at elevated pressure (e.g. from 0.5 to 5 bar).

The compounds of the general formulae (VI), (VII) and (IIa) are as species new and can be prepared like it is described above.

The compounds of the general formulae (III), (IIIa) and (IV) are known or can be prepared in analogy by published methods.

It has surprisingly been found that the compounds of the general formulae (I) and (Ia) are chloride channel types; moreover that they are able to block one or more channel blockers selectively.

AIRWAY DISEASE

Airway epithelial cell contain chloride channels which upon activation provide a selective export of chloride ions. It is known from the pathophysiology of cystic fibrosis that a defect in the cystic fibrosis transmembrane conductance regulator (CFTR)—a chloride channel, results in abnormal mucus secretions. This indicates a causal relationship between chloride transport and mucus seretion (in Cystic Fibrosis). Since mucus hypersecretion is a major clinical problem in airway diseases such as chronic bronchitis, bronchiectasis and asthma, it is probable that interference with chloride transport could regulate the secretion of airway mucus and thereby provide a significant improvement in the treatment of these diseases.

SECRETORY DIARRHOEA

The gut also contains epithelial cells with chloride channels very similar to those found in the airways. These are also of physiological importance. Secretory diarrhoea is a disease in which excessive chloride secretion is a major problem. This arises after infection of the gut by toxins such as cholera toxin. Over one million deaths a year are attributable to this disease. In addition diarrhoea, of lesser severity, is also a significant problem in diverse gastrointestinal disorders, such as inflammatory bowel disease. Thus providing a means of attenuating chloride secretion from cells chould substantially reduce the severity of the diarrhoea.

INFLAMMATION

Inflammatory cells such as neutrophils and lymphocytes also contain chloride channels which appear to be different from those found in epithelial cells. However, these channels appear to be activated in a number of pathophysiological processes. Accordingly compounds which block such channels may display pronounced anti-inflammatory effects.

This is confirmed by the following biological test system.

The most potent chloride channel blocker described to date is 2-(3-phenylpropyl)amino-5-nitrobenzoic acid (NPPB). This compound provides a suitable reference standard against which to judge other chloride channel blockers. It is the most effective of a series of chloride channel blockers and displays $IC_{50}$ values, at different chloride channels, in the range 10 nM–100 µM. In the test described below maximal inhibition of chloride efflux is observed at 300 µM, with 20% inhibition evident at the standard test concentration of 10 µg/ml.

The airway epithelial cell line 4MBr-5 was obtained from ATCC and cells were cultured in 35 mm diameter wells on six well plates until cell layers were confluent. Cells were loaded with $Na^{36}Cl$ solutions at 2.5 µCi/well after washing the cell monolayer free of 50 mM culture medium. Washing and loading were performed in Hepes buffer (pH 7.4) containing 130 mM NaCl, 5.4 mM KCl, 1.8 mM $CaCl_2$, 1.0 mM $NaH_2PO_4$, 0.8 mM $MgSO_4$ and 5.5 mM glucose. After a loading period of 60 minutes the cell layer was rapidly washed with 50 mM Hepes in 241 mM sucrose containing 1 nM $MgSO_4$ and the buffer replaced with 2 ml of $^{36}Cl^-$ free buffer containing 10 µg/ml test compound, or vehicle control. (Test compound was also present for the final ten minutes of the loading procedure). After 20 minutes efflux was stopped and the radioactivity remaining in the cells determined by liquid scintillation spectrometry after lysis of the cells. After subtraction of the counts found in cells treated with vehicle the increased counts were compared to the corresponding value observed with NPPB and expressed as a percentage of the maximal inhibition.

As can be seen from the data in Table A compounds of the inventions were more effective than NPPB at inhibiting chloride efflux.

TABLE A

| Example-No. | % Inhibition |
|---|---|
| 2/24 | 28.6 |
| 15/36 | 37.7 |
| 16/37 | 58.2 |
| 17/38 | 83.5 |
| 18/1 | 24 |
| 19/39 | 31.1 |
| 20/40 | 22.7 |
| 21/41 | 50.6 |
| 22/42 | 65 |
| 23/43 | 36.4 |

The compounds of the general formulae (I) and (Ia) can therefore be employed in medicaments for controlling acute and chronic inflammation, secretory diarrhoea, for example gastro-intestinal disorders and inflammatory bowel diseases and airway diseases such as chronic bronchitis, bronchiectasis or asthma.

The compounds according to the invention are preferably suitable for the treatment and prevention of acute and chronic inflammations of the airways, such as emphysema, alveolitis, shock lung, asthma, bronchitis, arteriosclerosis, arthrosis, inflammations of the gastro-intestinal tract and myocarditis, secretory diarrhoea.

The new active compounds can be converted in a known manner into the customary formulations, such as tablets, coated tablets, pills, granules, aerosols, syrups, emulsions, suspensions and solutions, using inert, nontoxic, pharmaceutically suitable excipients or solvents. In this connection, the therapeutically active compound should in each case be present in a concentration of about 0.5 to 90% by weight of the total mixture, i.e. in amounts which are sufficient in order to achieve the dosage range indicated.

The formulations are prepared, for example, by extending the active compounds with solvents and/or excipients, if appropriate using emulsifiers and/or dispersants, where, for example, in the case of the use of water as a diluent, organic solvents can be used as auxiliary solvents if appropriate.

Administration is carried out in a customary manner, preferably orally or parenterally, in particular perlingually or intravenously.

In the case of parenteral administration, solutions of the active compound can be employed using suitable liquid vehicles.

In general, it has proved advantageous on intravenous administration to administer amounts from about 0.001 to 10 mg/kg, preferably about 0.01 to 5 mg/kg of body weight to achieve effective results, and on oral administration the dosage is about 0.01 to 25 mg/kg, preferably 0.1 to 10 mg/kg of body weight.

In spite of this, it may be necessary to depart from the amounts mentioned, in particular depending on the body weight or the type of application route, on individual behaviour towards the medicament, the manner of its formulation and the time or interval at which administration takes place. Thus, in some cases it may be sufficient to manage with less than the abovementioned minimum amount, while in other cases the upper limit mentioned must be exceeded. In the case of administration of relatively large mounts, it is advisable to divide these into several individual doses over the course of the day.

STARTING COMPOUNDS

EXAMPLE I

Ethyl(4-hydroxy-5-(4-methoxyphenyl)cyclopent-1,3-dioxo-4-ene-2-yl)-2-oxoacetate

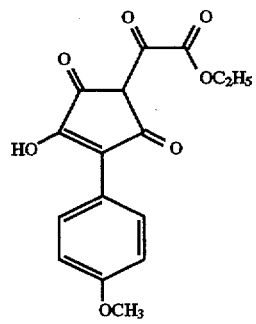

5.4 g (30.5 mmol) 4-methoxyphenylacetone and 8.15 ml (66 mmol) diethyloxalate were slowly added to a solution of 4.08 g (61 mmol) sodium ethoxide in ethanol at 5° C. After addition was complete the red solution was refluxed for 90 min, allowed to cool and then cooled to −10° C. and 20 ml 1:1 aqueous conc. sulphuric acid was added. The resultant yellow precipitate was collected by filtration and washed with water to give 3.8 g (38%). A sample was recrystallised from ethyl acetate to give bronze flakes m.p. 176°–178° C. $^1H$—NMR (90 MHz, $d_6$—DMSO)δ=1.41 (3 H, t, J=7.1 Hz), 3.84 (3 H, s); 4.42 (2 H, q, J=7 Hz); 6.93 (2 H, d, J=9.2 Hz); 7.45 (1 H, s); 8.20 (2 H, d, J=9.2 Hz).

EXAMPLE II

4-Hydroxy-5-(4-methoxyphenyl)cyclopent-1,3-dioxo-4-ene

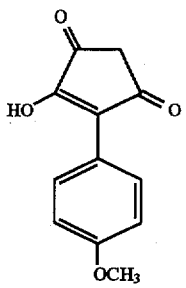

3.8 g (12 mmol) of the product of example I was refluxed for 90 min in 50 ml dilute hydrochloric acid. This was allowed to cool and the resultant red precipiate was collected by filtration and washed with water. Recrystallisation from aqueous ehtanol gave deep red needless 2.0 g (77%), m.p. 198°–200° C.

$^1$H—NMR (90 MHz, $d_6$—DMSO):δ=3.03 (2 H, s); 3.5 (1 H, br); 3.81 (3 H, s); 6.95 (2 H, dt, J=7.03, 2.1 Hz); 8.15 (2 H, dt, J=7.03, 2.1 Hz).

EXAMPLE III 3,5,5-Triethoxy-2-phenylcyclopent-2-enone

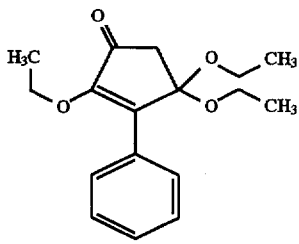

2.5 g (13.3 mmol) 4-hydroxy-5-phenylcyclopent-4-ene-1,3-dione were refluxed for 4 h with 6 ml (30 mmol) triethylorthoformate and a trace of p-toluene sulphonic acid in 50 ml ethanol. After cooling the ethanol was removed at reduced pressure and the residue neutralised and extracted with ether to give a deep red oil 167° C. 13.36 g (87%). This was used without further purification.

EXAMPLE IV

4-Phenylcyclopent-4-ene-1,3-dione

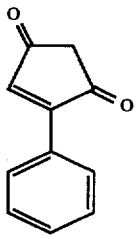

0,58 g (2 mmol) of the product of example III was dissolved in 20 ml dry toluene and cooled to –70° C., 4 ml 1M DIBAL (in hexane) was added and stirred for 2 h. This was quenched with methanol and allowed to warm to room temperature, evaporated to dryness and then stirred in a mixture of dilute HCl and THF for 1 h. This was extracted with ether and the extracts washed, dried and concentrated to give the dione as sticky orange needles 0.45 g (>100%). This was recrystallised from ethanol to give fine gold needles, m.p. 123°–124° C., 80 mg (24%).

$^1$H—NMR (90 MHz, CDCl$_3$):δ=3.1 (2 H, s); 7.38 (1 H, s); 7.4–7.6 (3 H, m); 7.8– 8.0 (2 H, m).

EXAMPLE V

2-Hydroxy-3-phenylcyclopent-2-ene-one

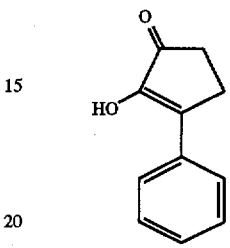

0.58 g (2 mmol) of the product of example III was dissolved in 15 ml dry THF and 2.2 ml 1M lithium aluminium hydride (in ether) was added and refluxed for 2 h. This was quenched with aqueous sodium sulfate filtered and concentrated to dryness, then stirred in a mixture of dilute HCl and THF overnight. This was extracted with ether and the extracts washed, dried and concentrated to give the enone as a yellow solid, 0.3 g. This was recrystallised from chloroform to give a yellow powder m.p. 79°–81° C.

$^1$H—NMR (90 MHz, CDCl$_3$): δ=2.3–2.8 (4 H, m); 7.0–7.6 (6 H, m).

PREPARATIONS EXAMPLES

EXAMPLE 1

4-Hydroxy-5-(4-methoxyphenyl)-2-(2-phenylethenyl)cyclopent-4-ene-1,3-dione

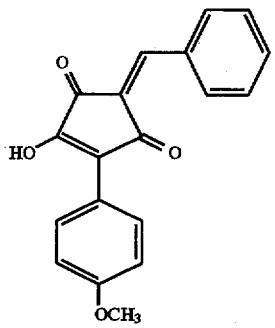

210 mg (1 mmol) of the product of example II and 120 μl (1.1 mmol) benzaldehyde were stirred together overnight in 1 ml methanol and 0.5 ml 1M sodium hydroxide. The suspension was acidified and the precipitate was filtered off and washed with water. Recrystallisation from ethyl acetate—pentane gave red needles 80 mg (26%) m.p. 226°–227° C.

$^1$H—NMR (90 MHz, $d_6$—DMSO): δ=3.87 (3 H, s); 6.97 (2 H, d, J=7.04 Hz);7.42 (1 H, s); 7.4–7.6 (4 H, m); 8.35 (2 H, d, J=7.04 Hz); 8.2–8.4 (2 H, m).

As described for Example 1, use of the requisite phenylacetone substituted by A" /D" and Aldehyde E"—CHO gives the products shown in table 1, 2 and 3.

TABLE 1

[structure with X, Y, A'' substituents on cyclopentene-1,2,4-trione with benzylidene]

| Example No. | X/Y | A'' |
|---|---|---|
| 2 | 4-CH₃O/H | H |
| 3 | 3,4-Cl | H |
| 4 | 4-t-Bu/H | H |
| 5 | 4-EtO/H | H |
| 6 | 2-Cl/H | H |
| 7 | 2-Me/H | H |
| 8 | 3-Me/H | H |
| 9 | 3,5-Me | H |
| 10 | 4-Br/H | H |
| 11 | 3-NO₂/H | H |
| 12 | 3-Br/H | H |
| 13 | 2-Br/H | H |
| 14 | 2,3-Cl | H |
| 15 | 2,4-Cl | H |
| 16 | 4-CF₃/H | H |
| 17 | 4-Ph/H | H |
| 18 | H/H | 4-MeO |
| 19 | H/H | 4-Cl |
| 20 | 4-NEt₂/H | H |
| 21 | 4-OCH₂Ph/H | H |
| 22 | 3,4-Cl | 4-MeO |
| 23 | 2-OH/H | H |

TABLE 2

(corresponding tautomers to compounds shown in table 1)

[tautomer structure with HO, X, Y, A'']

| Example No. | X/Y | A'' |
|---|---|---|
| 24 | 4-OCH₃/H | H |
| 25 | 3,4-Cl | H |
| 26 | 4-t-Bu/H | H |
| 27 | 4-Cl/H | H |
| 28 | 2-Me/H | H |
| 29 | 3-Me/H | H |
| 30 | 3,5-Me | H |
| 31 | 4-Br/H | H |
| 32 | 3-NO₂/H | H |
| 33 | 3-Br/H | H |
| 34 | 2-Br/H | H |
| 35 | 2,3-Cl | H |
| 36 | 2,4-Cl | H |
| 37 | 4-CF₃/H | H |
| 38 | 4-Ph/H | H |
| 39 | H/H | 4-Cl |
| 40 | 4-NEt₂/H | H |
| 41 | 4-OCH₂Ph/H | H |
| 42 | 3,4-Cl | 4-MeO |
| 43 | 2-OH/H | H |

TABLE 3

[structure with HO, phenyl, E'']

| Example-No. | E'' |
|---|---|
| 44 | 1-naphthyl |
| 45 | 2-naphthyl |
| 46 | 2-thienyl |
| 47 | 3-thienyl |

EXAMPLE 48

2-(2-[3,4-Dichlorophenyl]methyl)-4-hydroxy-5-(4-methoxyphenyl)cyclopent-4-ene-1,3-dione

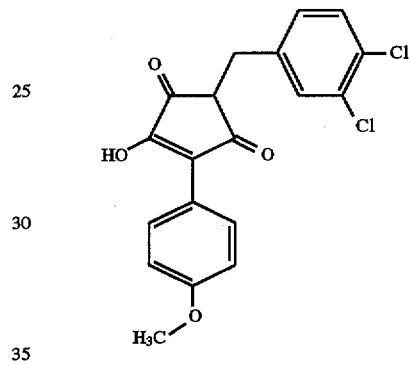

The product of example 42, 375 mg (1 mmol) was suspended in 50 ml methanol and 20 mg 10% palladium on charcoal was added. This was stirred under a hydrogen atmosphere for 18 hours. The resultant solution was filtered through Celite and concentrated to give the title compound, 0.35 g. This was recrystallised from ethyl acetate-pentane to give a yellow powder, 120 mg, m.p. 162°–164° C.

$^1$H—NMR (90 MHz, CDCl₃): δ=3.2 (1 H, br); 3.25 (2 H, d, J=5 Hz); 3.80 (1 H, t, J=5 Hz); 3.82 (3 H, s); 6.97 (2 H, d, J=8.8 Hz); 7.1–7.5 (3 H, m); 8.0 (2 H, d, J=8.8 Hz).

EXAMPLE 49

2-(2-[3,4-Dichlorophenyl]methylene)-4-phenylcyclopent-4-ene-1,3-dione

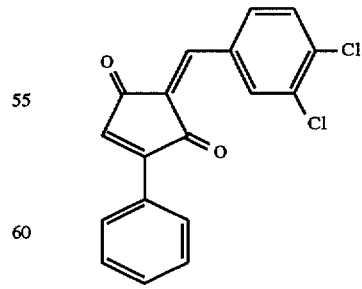

0.08 g (0.45 mmol) dione and 0.09 g (0.5 mmol) 3,4-dichlorobenzaldehyde were mixed in 2 ml methanol and 5 ml 1M sodium hydroxide and the suspension stirred overnight. Dilute HCl was added and the resultant precipitate was collected by filtration and the resultant solid was recrystallised from ethyl acetate to give the title compound as yellow needles m.p. 224°–225° C., 0.08 g.

$^1$H—NMR (90 MHz, d$^6$—DMSO): δ=7.0–8.1 (10 H, m).

EXAMPLE 50

2-(2-[3,4-Dichlorophenyl]methylene)-5-hydroxy-4-phenylcyclopent-4-enone

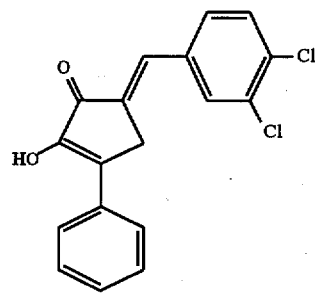

0.22 g (1.3 mmol) of the product of example V and 0.25 g (1.4 mmol) 3,4-dichlorobenzaldehyde were mixed in 3 ml methanol and 10 ml 1M sodium hydroxide and the suspension stirred overnight. Dilute HCl was added and the resultant pecipitate was collected by filtration and recrystallised from ethyl acetate to give the title compound as yellow needles m.p. 178°–180° C.; 0.1 g.

$^1$H—NMR (90 MHz, d$^6$—DMSO): δ=2.8 (2 H, s); 7.0–8.1 (10 H, m).

The compounds shown in table 4 are prepared in analogy to example 48–50.

TABLE 4

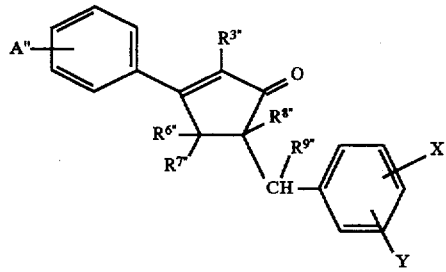

| Example-No. | A" | X/Y | R$^{3"}$ | R$^{6"}$/R$^{7"}$ | R$^{8"}$/R$^{9"}$ |
|---|---|---|---|---|---|
| 51 | 4-MeO | 3,4-Cl | OMe | =O | double bond |
| 52 | H | 4-t-Bu/H | OH | =O | H/H |

The compounds shown in Table 5 are prepared in analogy to the procedure of example 1.

TABLE 5

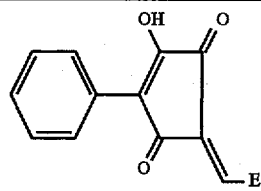

| Ex.-No. | E | Mp °C. | Yield (% of theory) |
|---|---|---|---|
| 53 | 4-hydroxyphenyl | 260 | 42 |
| 54 | pyridyl | 285 | 55 |
| 55 | 4'-nitrobiphenyl | 270 | 71 |

We claim:
1. Substituted cyclopentane- di- and -triones of the general formula

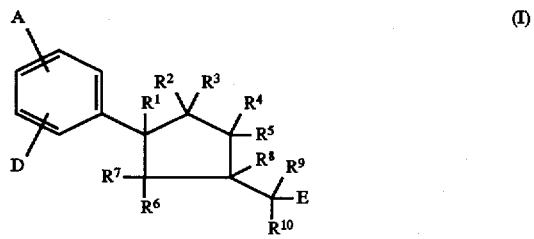

(I)

in which
A and D are identical or different and represent hydrogen, halogen, nitro, phenyl or straigth-chain or branched alkyl having up to 8 carbon atoms or represent a group of the formula —NR$^{11}$R$^{12}$, —CO$_2$R$^{13}$ or —O(CH$_2$)$_a$(CO$_2$)$_b$R$^{14}$
in which
R$^{11}$ and R$^{12}$ are identical or different and denote hydrogen, phenyl or straight-chain or branched alkyl having up to 6 carbon atoms, denotes hydrogen or straight-chain or branched alkyl having up to 8 carbon atoms, a denotes a number 0, 1,2, 3 or 4, b denotes a number 0 or 1, R$^{14}$ has the abovementioned meaning of R$^{13}$ and is identical or different to that or denotes phenyl,
R$^1$ represents hydrogen,
R$^2$ and R$^3$, R$^4$ and R$^5$ and/or R$^6$ and R$^7$ represent a residue of the formula =O, or two of the pairs have the abovementioned meaning and both substituents of the remaining pair, R$^2$ and R$^3$ or R$^4$ and R$^5$ or R$^6$ and R$^7$ represent hydrogen, or
R$^1$ and R$^2$ or R$^1$ and R$^7$ or R$^2$ and R$^4$ together represent a double bond and in these cases,
R$^3$,R$^5$ and R$^6$ respectively represent hydrogen hydroxyl or a straight-chain or branched alkoxy having up to 6 carbon atoms, $R^8$ and $R^9$ represent hydrogen,
or
$R^8$ and $R^9$ together represent a double bond,
$R^{10}$ has the abovementioned meaning of A or D and is identical or different to that,
E represents a 5 to 7 membered, aromatic heterocycle having up to 3 heteroatoms from the series comprising N, S and O and to which a phenyl ring can be fused, or represents aryl having up to 6 to 10 carbon atoms and wherein all rings are optionally monosubstituted to trisubstituted by identical or different substitutents from the series comprising halogen, nitro, trifluoromethyl, phenyl or straight-chain or branched alkyl having up to 6 carbon atoms or by a group of the formula —$NR^{15}R^{16}$, —$CO_2R^{17}$ or —$O(CH_2)_d$—$(CO_2)_eR^{18}$, in which $R^{15}$ and $R^{16}$ have the abovementioned meaning of $R^{11}$ and $R^{12}$ and are identical or different to that, $R^{17}$ has the abovementioned meaning of $R^{13}$ and is identical or different to that $R^{18}$ has the above mentioned meaning of $R^{14}$ and is identical or different to that, d denotes a number 0, 1, 2, 3 or 4, e denotes a number 0 or 1, and their tautomers, racemates, enantiomers, diastereomers and salts,
with the exception of
1,2,4-cyclopentanetrione, 3-[(4-chlorophenyl)methyl]-5-phenyl, 1,2,4-cyclopentanetrione, 3-[(4-chloro-3-nitrophenyl)methyl]-5-phenyl, 1,2,4-cyclopentanetrione, 3-[(4-chlorophenyl)methylene]-5-phenyl, 4-cyclopentene-1,3-dione, 4-ethoxy-5-phenyl-2-(phenylmethylene)-(Z) and (E) 4-cyclopentene-1,3-dione, 2-[(4-chlorophenyl)methyl]-4-hydroxy-5-phenyl 4-cyclopentene-1,3-dione, 2-[4-(chlorphenyl)methylene)-4-hydroxy-5-phenyl 2- (4-chloro-3-nitrobenzyliden)-4-hydroxy-5-phenyl-cyclopent-4-ene-1,3-dion 3-(4-nitro-benzylidene)-5-phenyl-cyclopentane-1,2,4-trione 3-(4-methyl-benzylidene)-5-phenyl-4-cyclopentane-1,2,4-trione 3-benzylidene-5-phenyl-cyclopentane-1,2,4-trione.

2. A process for the preparation of substituted cyclopentane- di- and -triones according to claim 5 characterized in that

[A] compounds of the general formula (II)

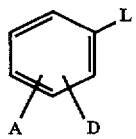

(II)

in which
A and D have the meaning already given,
and
L stands for the residue

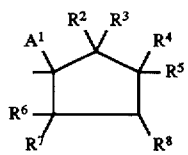

are reacted with compounds of the general formulae (III) or (IIIa)

(III)

(IIIa)

in which
E has the meaning given,
and
T denotes halogen,
in the presence of an inert solvent and optionally in presence of a base or an auxiliary,
or
[B] in the case of the triones and their tautomers compounds of the general formula (IV)

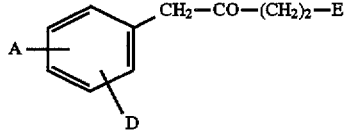

(IV)

in which
A, D and E have the abovementioned meaning,
are reacted with diethyloxalate/$NaOC_2H_5$ by cyclisation after decarboxylation,
and
if appropriate in the case of $R^8/R^9$=hydrogen,
compounds of the general formulae (I) with a corresponding double bond are hydrogenated
and in the case of $R^3$, $R^5$ or $R^6 \neq OH$, the corresponding hydroxyl compounds are etherified.

3. A composition comprising at least one substituted cyclopentane- di- or -trione according to claim 1 and a pharmacologically acceptable diluent.

4. A composition according to claim 3 as chloride channel blocker.

5. A composition according to claim 4 for controlling airway diseases, secretory diarrhoea and inflammatory diseases.

6. A process for the preparation of compositions according to claim 3 characterized in that the active ingredient together with the pharmacologically acceptable diluent is transferred in a form suitable for administration.

7. A method for controlling airway disease, secretory diarrhoea and inflammatory diseases which comprises administering to a host in need thereof an effective amount of a substituted cyclopentane- di- and -trione of the formula

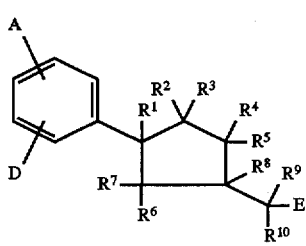

(I)

in which
A and D are identical or different and represent hydrogen, halogen, nitro, phenyl or straigth-chain or branched alkyl having up to 8 carbon atoms or represent a group of the formula —$NR^{11}R^{12}$, —$CO_2R^{13}$ or
—$O(CH_2)_a(CO_2)_bR^{14}$
in which
$R^{11}$ and $R^{12}$ are identical or different and denote hydrogen, phenyl or straight-chain or branched alkyl having up to 6 carbon atoms, $R^{13}$ denotes hydrogen or straight-chain or branched alkyl having up to 8 carbon atoms, a denotes a number 0, 1, 2, 3 or 4, b denotes a number 0 or 1, $R^{14}$ has the abovementioned meaning of $R^{13}$ and is identical or different to that or denotes phenyl, $R^1$ represents hydrogen, $R^2$ and $R^3$, and $R^5$ and/or $R^6$ and $R^7$ represent a residue of the formula $=O$, or two of the pairs have the abovementioned meaning and both substitutents of the remaining pair;

$R^2$ and $R^3$ or $R^4$ and $R^5$ or $R^6$ and $R^7$ represent hydrogen, or $R^1$ and $R^2$ or $R^1$ and $R^7$ or $R^2$ and $R^4$ together represent a double bond and in these cases, $R^3$, $R^5$ and $R^6$ respectively represent hydrogen, hydroxyl or a straight-chain or branched alkoxy having up to 6 carbon atoms, $R^8$ and $R^9$ represent hydrogen, or $R^8$ and $R^9$ together represent a double bond, $R^{10}$ has the abovementioned meaning of A or D and is identical or different to that, E represents a 5 to 7 membered, aromatic heterocycle having up to 3 heteroatoms from the series comprising N, S and O and to which a phenyl ring can be fused, or represents aryl having up to 6 to 10 carbon atoms and wherein all rings are optionally monosubstituted to trisubstituted by identical or different substitutents from the series comprising halogen, nitro, trifluoromethyl, phenyl or straight-chain or branched alkyl having up to 6 carbon atoms or by a group of the formula $-NR^{15}R^{16}$, $-CO_2R^{17}$ or $-O(CH_2)_d-(CO_2)_eR^{18}$ in which $R^{15}$ and $R^{16}$ have the abovementioned meaning of $R^{11}$ and $R^{12}$ and are identical or different to that, $R^{17}$ has the abovementioned meaning of $R^{13}$ and is identical or different to that $R^{18}$ has the above mentioned meaning of $R^{14}$ and is identical or different to that, d denotes a number 0, 1, 2, 3 or 4, e denotes a number 0 or 1, or an isomer or salt thereof.

8. The method according to claim 7, wherein

A and D are identical or different and represent hydrogen, fluorine, chlorine, bromine, nitro, phenyl or straigth-chain or branched alkyl having up to 6 carbon atoms or represent a group of the formula $-NR^{11}R^{12}$, $-CO_2R^{13}$ or $-O(CH_2)_d(CO_2)_bR^{14}$ in which $R^{11}$ and $R^{12}$ are identical or different and denote hydrogen, phenyl or straight-chain or branched alkyl having up to 4 carbon atoms, $R^{13}$ denotes hydrogen or straight-chain or branched alkyl having up to 6 carbon atoms, a denotes a number 0, 1, 2, 3 or 4, b denotes a number 0 or 1, $R^{14}$ has the abovementioned meaning of $R^{13}$ and is identical different to that or denotes phenyl, $R^1$ represents hydrogen, $R^2$ and $R^3$, $R^4$ and $R^5$ and/or $R^6$ and $R^7$ represent a residue of the formula $=O$, or two of the pairs have the abovementioned meaning and both substituents of the remaining pair, $R^2$ and $R^3$ or $R^4$ and $R^5$ or $R^6$ and $R^7$ represent hydrogen or $R^1$ and $R^2$ or $R^1$ and $R^7$ or $R^2$ and $R^4$ together represent a double bond and in these cases $R^3$, $R^5$ and $R^6$ respectively represent hydrogen hydroxyl or a straight-chain or branched alkoxy having up to 4 carbon atoms, $R^8$ and $R^9$ represent hydrogen, or $R^8$ and $R^9$ together represent a double bond or $R^{10}$ has the abovementioned meaning of A or D and is identical or different to that, E represents thienyl, pyridyl, naphthyl or phenyl, which are optionally monosubstituted to trisubstituted by identical or different substitutents from the series comprising fluorine, chlorine, bromine, nitro, trifluoromethyl, phenyl or straight-chain or branched alkyl having up to 4 carbon atoms or by a group of the formula $-NR^{15}R^{16}$, $-CO_2R^{17}$ or $-O(CH_2)_d-(CO_2)_eR^{18}$, in which $R^{15}$ and $R^{16}$ have the abovementioned meaning of $R^{11}$ and $R^{12}$ and are identical or different to that, $R^{17}$ has the abovementioned meaning of $R^{13}$ and is identical or different to that $R^{18}$ has the above mentioned meaning of $R^{14}$ and is identical or different to that, d denotes a number 0, 1, 2, 3 or 4, e denotes a number 0 or 1, or an isomer or salt thereof.

9. The method according to claim 7, wherein

A and D are identical or different and represent hydrogen, fluorine, chlorine, bromine, nitro, phenyl or straigth-chain or branched alkyl having up to 5 carbon atoms or represent a group of the formula $-NR^{11}R^{12}$, $-CO_2R^{13}$ or $-O(CH_2)_a(CO_2)_bR^{14}$ in which $R^{11}$ and $R^{12}$ are identical or different and denote hydrogen, phenyl or straight-chain or branched alkyl having up to 3 carbon atoms, $R^{13}$ denotes hydrogen or straight-chain or branched alkyl having up to 5 carbon atoms, a denotes a number 0, 1, 2, 3 or 4, b denotes a number 0 or 1, $R^{14}$ has the abovementioned meaning of $R^{13}$ and is identical or different to that or denotes phenyl, $R^1$ represents hydrogen, $R^2$ and $R^3$, $R^4$ and $R^5$ and/or $R^6$ and $R^7$ represent a residue of the formula $=O$, or two of the pairs have the abovementioned meaning and both substituents of the remaining pair, $R^2$ and $R^3$ or $R^4$ and $R^5$ or $R^6$ and $R^7$ represent hydrogen, or $R^1$ and $R^2$ or $R^1$ and $R^7$ or $R^2$ and $R^4$ together represent a double bond and in these cases, $R^3$, $R^5$ and $R^6$ respectively represent hydrogen hydroxyl or a straight-chain or branched alkoxy having up to 3 carbon atoms, $R^8$ and $R^9$ represent hydrogen, or $R^8$ and $R^9$ together represent a double bond, $R^{10}$ has the abovementioned meaning of A or D and is identical or different to that, E represents thienyl, pyridyl, naphthyl or phenyl, which are optionally monosubstituted to trisubstituted by identical or different substitutents from the series comprising fluorine, chlorine, bromine, trifluoromethyl, nitro, phenyl or straight-chain or branched alkyl having up to 4 carbon atoms or by a group of the formula $-NR^{15}R^{16}$, $-CO_2R^{17}$ or $-O(CH_2)_d-(CO_2)_eR^{18}$, in which $R^{15}$ and $R^{16}$ have the abovementioned meaning of $R^{11}$ and $R^{12}$ and are identical or different to that, $R^{17}$ has the abovementioned meaning of $R^{13}$ and is identical or different to that $R^{18}$ has the above mentioned meaning of $R^{14}$ and is identical or different to that, d denotes a number 0, 1, 2, 3 or 4, e denotes a number 0 or 1, or an isomer or salt thereof.

10. The method according to claim 7, wherein

A and D are identical or different and represent hydrogen, phenyl, chlorine or methoxy, or a salt thereof.

* * * * *

UNITED STATES PATENT AND TRADEMARK OFFICE
CERTIFICATE OF CORRECTION

PATENT NO. : 5,684,205
DATED : November 4, 1997
INVENTOR(S) : Norman, et al.

It is certified that error appears in the above-indentified patent and that said Letters Patent is hereby corrected as shown below:

Col. 18, line 50   Before " denotes " insert -- $R^{13}$ --

Col. 19, line 44   Delete claim " 5 " and substitute -- 1 --

Col. 21, line 8    After " $R^3$, " insert -- $R^4$ --

Col. 21, line 64   Before " different " insert -- or --

Signed and Sealed this

Twenty-fourth Day of November, 1998

Attest:

BRUCE LEHMAN

*Attesting Officer*   *Commissioner of Patents and Trademarks*